(12) United States Patent
Jänichen et al.

(10) Patent No.: US 7,728,168 B2
(45) Date of Patent: Jun. 1, 2010

(54) PROCESS TO MANUFACTURE 4-METHOXYBENZOIC ACID FROM HERBAL ANETHOLE AND THE USE OF 4-METHOXYBENZOIC ACID IN COSMETIC AND DERMATOLOGIC PRODUCTS AS WELL AS FOODSTUFFS

(75) Inventors: Jan Jänichen, Hamburg (DE); Wilfried Petersen, Hamburg (DE); Rudolf Jenny, Allmendingen (CH); Markus Nobis, Lyss (CH)

(73) Assignee: Dr. Straetmans Chemische Produkte GmbH, Hamburg (DE)

( * ) Notice: Subject to any disclaimer, the term of this patent is extended or adjusted under 35 U.S.C. 154(b) by 0 days.

(21) Appl. No.: 12/263,633

(22) Filed: Nov. 3, 2008

(65) Prior Publication Data

US 2009/0131712 A1 May 21, 2009

(30) Foreign Application Priority Data

Nov. 19, 2007 (EP) ................................. 07120946

(51) Int. Cl.
C07C 51/23 (2006.01)
C07C 65/00 (2006.01)
(52) U.S. Cl. ....................... 562/421; 562/473
(58) Field of Classification Search .................. None
See application file for complete search history.

(56) References Cited

U.S. PATENT DOCUMENTS

| 2,916,499 | A | * | 12/1959 | Blair | 549/436 |
| 3,799,940 | A | * | 3/1974 | Mains et al. | 549/431 |
| 4,940,808 | A | * | 7/1990 | Schulz et al. | 549/436 |
| 2004/0167195 | A1 | | 8/2004 | Muller | 514/400 |

FOREIGN PATENT DOCUMENTS

EP 1 325 731 7/2003

OTHER PUBLICATIONS

Carey and Sunberg "Advanced Organic Chemistry, second edition, Part B: Reactions and Synthesis" 1985, Plenum Publishing Corporation, New York, pp. 510-514.*
Dodd et al., Synthesis (1993), (3), 295-7.*
Briner et al. Researches On the Infrared Absorption Spectra of Ozonides. XV. Ozonation of trans- and cis-anethole; Autoxidation, Accelerated By Ozone, of Anisic Aldehyde Helvetica Chimica Acta, 41, 2178-85.*
Carey and Sundberg: "Advanced Organic Chemistry, Second Edition, Part B: Reactions and Synthesis." 1985, Plenum Publishing Corporation, New York, XP002476889.
Liu, Lihua et al. "Preparation of p-anisic Aldehyde By Ozonization." Database CA [Online]. Chemical Abstracts Service, Columbus, Ohio, US; XP002476890. Gefunden im STN, Database accession No. 1998: 290975. *Zusammenfassung* & Guangxi Huagong, 26 (1), 11-14.
Briner, E., et al.: "Researches On the Infrared Absorption Spectra of Ozonides. XV.Ozonation of trans- and cis-anethole; Autoxidation, Accelerated By Ozone, of Anisic Aldehyde." Helvetica Chimica Acta, 41, 2178-85. XP002476887.
Carey and Sundberg: "Advanced Organic Chemistry, Second Edition, Part B: Reactions and Synthesis" 1985, Plenum Publishing Corporation, New York pp. 510-514.
Henne, A.L. and P. Hill, "The Preparation of Aldehydes, Ketones, and Acids by Ozone Oxidation" Journal of the American Chemical Society, vol. 65, 1943, pp. 752-754.

* cited by examiner

Primary Examiner—Karl J Puttlitz
(74) Attorney, Agent, or Firm—Roberts & Roberts, LLP

(57) ABSTRACT

A process to manufacture 4-methoxybenzoic acid from anethole. This raw material can be obtained from a variety of plant materials and thus offers a renewable alternative to fossil raw materials. Another aspect of the present invention is the use of 4-methoxybenzoic acid gained from vegetal anethole as raw material in cosmetic and dermatologic products and/or aroma components in foodstuffs.

9 Claims, No Drawings

PROCESS TO MANUFACTURE 4-METHOXYBENZOIC ACID FROM HERBAL ANETHOLE AND THE USE OF 4-METHOXYBENZOIC ACID IN COSMETIC AND DERMATOLOGIC PRODUCTS AS WELL AS FOODSTUFFS

BACKGROUND OF THE INVENTION

1. Field of the Invention

The invention concerns a production process for 4-methoxybenzoic acid and its use.

2. Description of the Related Art

The search for alternatives to exploit fossil resources to generate energy or to produce chemical raw materials has increasingly gained importance in recent years. Searching for alternative sources of raw materials, plants are of significant importance as they provide complex raw materials in renewable form, which in addition do not have an impact on the climate when being degraded. Also against the background of an increasing awareness of nature by a growing number of people and the limited amount of fossil sources a constantly flourishing market for products based on natural raw materials has developed just as a growing industry to gain and manufacture them.

Evaluating raw materials ecologically, apart from their origin, their possible processing plays a vital role. Taking a complex view, the use of energy resources and the production of waste products during the process have to be considered and included in an eco-balance of a raw material. The natural origin of raw materials in use is in the meantime being especially appreciated by various industries and obligatory standards of winning and processing natural substrates are being defined. Thus e.g. in the cosmetics as well as foodstuffs industry a fast growing number of suppliers offering natural products has evolved, regulating the raw materials in use and the processes to gain and manufacture them according to strict standards.

p-methoxybenzoic acid (INCI: p-anisic acid) has become increasingly important as multifunctional raw material in the cosmetics industry as well as in the foodstuffs industry in recent years. Apart from its main functions as masking agent and aroma component, the interesting characteristics of this raw material to biologically stabilize cosmetic and dermatologic formulations and as active component against specific germs in skin- and hair-care products has created a great interest in this raw material. p-methoxybenzoic acid can be found in various plants such as anise or fennel for example. However, isolating this raw material from these sources is of no interest due to the minor quantities. Currently the product used by the cosmetic and foodstuffs industry is manufactured from petrochemical raw materials.

SUMMARY OF THE INVENTION

The invention provides a process for the manufacturing of 4-methoxybenzoic acid from 1-methoxy-4-(1-propenyl) benzene (anethole) comprising transforming the anethole into an ozonide, which subsequently is converted into a 4-methoxybenzoic acid by oxidative work-up.

DESCRIPTION OF THE INVENTION

Against this background it was the task of the present invention to develop an ecologically reasonable process to produce p-methoxybenzoic acid from a renewable source taking chemical conversion processes into consideration which meet the requirements of producers of natural products, especially cosmetic products.

Unexpectedly, it was found, that this task could be solved in an excellent manner by converting natural anethole with ozone and subsequent in-situ oxidative treatment.

Anethole is a very common natural substance which can be isolated by extraction or distillation from various plants. Without limiting the presented patent application to special raw materials, the main sources of anethole, which can be used according to this invention, are based on the oils of the star anise (*Illicium Verum*) or the Indian basil (*Ocimum Tenuiflorum*). Its characteristic anise smell and its low toxicity make natural anethole a flavoring agent which is used in the foodstuffs industry in large quantities.

From a chemist's point of view, natural anethole consists of a cis/trans-mixture of 1-methoxy-4-(1-propenyl)benzene, with the trans-isomer present at 98% clearly being dominant. While this methoxy group in the molecule is chemically relatively inert, the olefin double bond offers possibilities for a variety of chemical modifications.

The conversion of organic substrates with ozone presents an especially interesting method of modifying chemical structures as it is environmentally friendly. The reactive species ozone can be produced electrochemically from oxygen and the formation of problematic halogen-organic reaction- or by-products can be excluded if the used substrates do not contain halogens.

The advantages of ozone are also exploited in environmental engineering, where it is used increasingly e.g. in wastewater treatment or chlorine-free water sterilization.

In recent years the number of patent applications depicting the use of ozone has increased continuously.

EP1362840, for example, describes the production of aromatic acids by catalytic oxidation of methylbenzenes with ozone and transition metal catalysts. In this reaction the ozone functions as oxidizing agent which together with the transition metal catalyst converts the methyl group into a carboxyl group. EP1569885 claims the in-situ conversion of ozonides from alkenes to aldehydes and ketones also using the help of transition metal catalysts. An elegant way of forming ketones is the ozonolysis of allylic alcohols which described in application EP1710224.

The conversion of alkenes with ozone is well described in detail in the relevant organic chemical literature. In a [2+3]-cyclo addition, the reaction leads to an ozonide which can be transformed to various functionalities depending on its subsequent treatment. In many cases the ozone's high activity, however, leads to by-products, which can only be controlled by exactly defined reaction conditions. Furthermore, the ozonide constitutes a highly energetic intermediate which requires high safety measurements during the process.

Considering these preconditions a process was now identified which is able to convert an ozonide, which was formed from a natural mixture of cis- and trans-anethole in a surprisingly clean reaction into a 4-methoxy-benzoic acid, in-situ and in a controllable process without adding further catalysts.

In a preferred process ozone is added to the natural anethole at temperatures between −30° C. and +30° C. in a solvent of the group of C1-6 mono- or dicarboxylic acids, esters, water, acetone, or C1-6 alcohols, or in mixtures of the mentioned solvents. The conversion in ethanol is especially preferred. Preferred is the formation of the ozonide from 1-methoxy-4-(1-propenyl) benzene (anethole) at temperatures between −10° C. and +10° C. in ethanol.

According to the invention the in-situ conversion of the formed ozonide into 4-methoxybenzoic acid is carried out by an oxidative cleavage of the ozonide with an alkaline hydrogen peroxide solution. Especially advantageous and safe proved to be a process in which a mixture of the ozonide of 1-methoxy-4-(1-propenyl) benzene and a concentrated hydrogen peroxide solution is added to a warm, diluted alkali- or earth-alkali hydroxide solution. Sodium- or potassium hydroxide turned out to be especially suitable. Unexpectedly, a diluted mixture of the ozonide of 1-methoxy-4-(1-propenyl) benzene and hydrogen peroxide in alcohol proved to be thermally stable at a wide range of temperatures. The exothermal cleavage of the ozonide of the 1-methoxy-4-(1-propenyl) benzene and the subsequent oxidation according to this invention are carried out fast and without concentrating reactive by-products, resulting in a good reaction control and high process safety. Adding the mixture of ozonide and hydrogen peroxide to a 30-105° C. warm 1-25% sodium hydroxide solution at a constant temperature proved to be especially advantageous.

The 4-methoxy-benzoic acid can be precipitated from the alkaline reaction mixture in high purity with the help of mineral acids. Preferred mineral acids according to this invention are to be chosen preferably from the group of sulfuric or phosphoric acid. Adding sulfuric acid to precipitate the 4-methoxy-benzoic acid at a pH-value between 3 and 6 is especially advantageous. If desired, traces of aldehydes or other by-products can be eliminated by using activated carbon. The yield of 4-methoxybenzoic acid obtained according to this process is in the range of 70 to 80% of the theory.

The final product according to the invention is characterized by a high purity which fully complies with the requirements for raw materials used in the cosmetics and foodstuffs industries. 4-methoxybenzoic acid produced according to the invention's methods is particularly suitable for perfuming, aromatizing, regulating pH-values, anti-inflammatory treatment and/or combating micro-organisms in cosmetic or dermatologic products, as active ingredient against specific pathogenic germs in skin treating products and/or for aromatizing and/or preserving foodstuffs or other perishable products. Comparative studies using 4-methoxybenzoic acid of petrochemical sources show no difference whatsoever in this product's described characteristics.

What is claimed is:

1. A process for the manufacture of 4-methoxybenzoic acid comprising converting 1-methoxy-4-(1-propenyl) benzene into an ozonide of 1-methoxy-4-(1-propenyl) benzene, and then subsequently oxidizing the ozonide with an alkaline hydrogen peroxide solution to thereby form a reaction mixture comprising 4-methoxybenzoic acid.

2. The process according to claim 1 wherein the 1-methoxy-4-(1-propenyl) benzene is obtained by an extraction or distillation process from plant material.

3. The process according to claim 1 comprising formation of the ozonide from 1-methoxy-4-(1-propenyl) benzene at temperatures between −30° C. and +30° C. in a solvent comprising C1-6 mono- or dicarboxylic acids, esters, water, acetone, C1-6 alcohols, or mixtures of these solvents.

4. The process according to claim 1 comprising the formation of the ozonide from 1-methoxy-4-(1-propenyl) benzene at temperatures between −10° C. and +10° C. in ethanol.

5. The process according to claim 1 wherein the oxidizing of the ozonide of 1-methoxy-4-(1-propenyl) benzene is achieved by mixing the ozonide with an alkaline hydrogen peroxide solution to form a mixture, and subsequently adding this mixture to a diluted solution of an alkali- or earth-alkali hydroxide at 30-105° C.

6. The process according to claim 1 wherein the oxidizing of the ozonide of 1-methoxy-4-(1-propenyl) benzene is achieved by mixing the ozonide with an alkaline hydrogen peroxide solution to form a mixture, and subsequently adding the mixture to a 1-25% aqueous sodium hydroxide solution at 60-80° C.

7. The process according to claim 1 wherein the 4-methoxybenzoic acid is subsequently isolated from the reaction mixture by precipitation with a mineral acid in a pH-range of 3-6 and filtration.

8. The process according to claim 7 further comprising treating the reaction mixture with activated carbon to remove by-products after the oxidizing of the ozonide and before precipitating with the mineral acid.

9. The process according to claim 8 further comprising purifying the 4-methoxy-benzoic acid gained from precipitation with the mineral acid, by dissolution in diluted sodium hydroxide, treatment with activated carbon and precipitating with sulfuric acid.

* * * * *